United States Patent
Chen et al.

(10) Patent No.: US 12,264,370 B2
(45) Date of Patent: Apr. 1, 2025

(54) SOYASAPONIN-RELATED KOMPETITIVE ALLELE-SPECIFIC POLYMERASE CHAIN REACTION MARKERS AND APPLICATION THEREOF

(71) Applicant: Jiangsu Academy of Agricultural Sciences, Jiangsu (CN)

(72) Inventors: Huatao Chen, Jiangsu (CN); Hongmei Zhang, Jiangsu (CN); Xiaoqing Liu, Jiangsu (CN); Wei Zhang, Jiangsu (CN); Qiong Wang, Jiangsu (CN)

(73) Assignee: Jiangsu Academy of Agricultural Sciences, Nanjing (CN)

( * ) Notice: Subject to any disclaimer, the term of this patent is extended or adjusted under 35 U.S.C. 154(b) by 0 days.

(21) Appl. No.: 18/480,799

(22) Filed: Oct. 4, 2023

(65) Prior Publication Data

US 2024/0102112 A1    Mar. 28, 2024

Related U.S. Application Data

(63) Continuation of application No. PCT/CN2022/131935, filed on Nov. 15, 2022.

(30) Foreign Application Priority Data

Sep. 16, 2022 (CN) .......................... 202211126454.4

(51) Int. Cl.
C12Q 1/6895 (2018.01)
C12Q 1/6858 (2018.01)

(52) U.S. Cl.
CPC ......... *C12Q 1/6895* (2013.01); *C12Q 1/6858* (2013.01); *C12Q 2600/13* (2013.01)

(58) Field of Classification Search
None
See application file for complete search history.

(56) References Cited

FOREIGN PATENT DOCUMENTS

| | | |
|---|---|---|
| CN | 101342227 A | 1/2009 |
| CN | 105112546 A | 12/2015 |
| CN | 109022542 A | 12/2018 |
| CN | 112877467 A | 6/2021 |
| KR | 20190127445 A | 11/2019 |

OTHER PUBLICATIONS

Gao, A SNP-Based Molecular Barcode for Characterization of Common Wheat, PLoS ONE, 11(3): 1-12, 2016. (Year: 2016).*
Park, Characterization of a New Allele of the Saponin-Synthesizing Gene Sg-1 in Soybean, Crop Science, 56: 385-391, 2016. (Year: 2016).*
GenBank Accession No. AB628090.1, Glycine max GmSg-1 gene, complete sequence, 2012. (Year: 2012).*
Tang Wei, et al., "Genome-wide Association Analysis of Saponin Content in Soybean Seeds," Soybean Science, Jun. 30, 2023, pp. 291-297, vol. 42, No. 3. (doi: 10.11861/j.issn.1000-9841.2023.03.0291) Related claims: 1-7.
Tan Meixia et al., "Visual detection for the absence of group A saponins in soybeans based on Gap-LCR reactions," Journal of Shanxi Agricultural University (Natural Science Edition), Dec. 31, 2020, pp. 19-26, vol. 40, No. 2. (doi: 10.13842/j.cnki.issn1671-8151.201912013)Related claims: 1-7.
Neelam R. Redekar et al., "Genetic interactions regulating seed phytate and oligosaccharides in soybean (*Glycine max* L.)" PLOS ONE, Jun. 25, 2020, pp. 1-18. Related claims: 1-7.
Notification to Grant Patent for China Application No. 202211126454.4, mailed Aug. 24, 2023.
First Search Report for China Application No. 202211126454.4, dated Aug. 23, 2023.
Tian Jun et al., "QTL analysis of soyasaponin content in soybean," Journal of Northeast Agricultural University, Oct. 2010, vol. 41, No. 10.
Wang Weidong, "Research Advances on Component Biosynthesis Metabolism and Genetic Improvement of Soyasaponins," Molecular Plant Breeding, Dec. 2016, pp. 3,561-3,569, vol. 14, No. 2.
Takashi Sayama et al., "TheSg-1Glycosyltransferase Locus Regulates StructuralDiversity of Triterpenoid Saponins of Soybean," The Plant Cell, May 2012, pp. 2,123-2,138, vol. 24.
Zhao Qiao-Ling et al., "Type Analysis of Saponin and Gene Expression of Key Enzyme in Shanxi Soybeans," Biotechnology Bulletin, Aug. 2017, pp. 73-80, vol. 33, No. 8.
International Search Report and Written Opinion for PCT/CN2022/131935, mailed Jun. 16, 2023.

* cited by examiner

*Primary Examiner* — Angela M. Bertagna
*Assistant Examiner* — Carolyn L Greene
(74) *Attorney, Agent, or Firm* — Pilloff Passino & Cosenza LLP; Rachel Pilloff; Sean Passino (57) ABSTRACT

Soyasaponin-related Kompetitive Allele Specific polymerase chain reaction (KASP) markers and an application thereof are provided in the present application, belonging to the technical field of molecular breeding. The KASP markers include one or two of S07_43139773G/T, and S07_43139033A/G; the S07_43139773G/T comprises a base of G/T at a position of 43139773 bp on chromosome 7 of a soybean genome, the S07_43139033A/G comprises a base of A/G at a position of 43139033 bp on the chromosome 7 of the soybean genome. The KASP markers are applied to improve soyasaponin germplasm breeding.

1 Claim, 11 Drawing Sheets

Specification includes a Sequence Listing.

SOYASAPONIN-RELATED KOMPETITIVE ALLELE-SPECIFIC POLYMERASE CHAIN REACTION MARKERS AND APPLICATION THEREOF

CROSS-REFERENCE TO RELATED APPLICATIONS

This application is a continuation of PCT/CN2022/131935, filed Nov. 15, 2022 and claims priority of Chinese Patent Application No. 202211126454.4, filed on Sep. 16, 2022, the entire contents of which are incorporated herein by reference.

INCORPORATION BY REFERENCE STATEMENT

This statement, made under Rules 77(b)(5)(ii) and any other applicable rule incorporates into the present specification of an XML file for a "Sequence Listing XML" (see Rule 831(a)), submitted via the USPTO patent electronic filing system or on one or more read-only optical discs (see Rule 1.52(e)(8)), identifying the names of each file, the date of creation of each file, and the size of each file in bytes as follows:
File name: 347-074-9220 Sequence Listing
Creation date: 25 Sep. 2023
Byte size: 6,346

TECHNICAL FIELD

The present application belongs to the technical field of molecular breeding, and in particular relates to soyasaponin-related Kompetitive Allele-specific polymerase chain reaction (KASP) markers and an application thereof.

BACKGROUND

Soyasaponins, also known as soybean saponins, are a class of compounds derived from the seeds of soybeans and other leguminous plants, with molecules formed by condensation of oligosaccharides and oleanocene triterpenes to form a class of compounds. Currently, soyasaponins have been identified by chemical study, namely soyasaponin A, soyasaponin B, soyasaponin C, soyasaponin D, soyasaponin E, with the soyasaponin A, soyasaponin B, and soyasaponin E naturally available. Studies have also shown that soyasaponins possess a variety of physiological properties, including anti-lipid oxidation, anti-free radicals, enhancing immune regulation, anti-tumour, anti-virus and so on, and have a broad market prospect for application in food, pharmaceuticals, cosmetics and other fields.

Despite the important contribution of soyasaponins to human health, the current exploitation of soybean resources is relatively low, with few varieties of special-purpose soybeans, suggesting a good prospect for development for the cultivation of special-purpose soybeans. Soyasaponins are regulated by multiple genes and are vulnerable to external environmental factors such as soil environment and climate change. The conventional screening of saponins in each soybean germplasm involves a long identification period, high costs, considerable time-consumption and labour-intensity, and fails to meet the demand for stable and efficient screening.

SUMMARY

In view of these, the present application provides soyasaponin-related Kompetitive Allele-specific polymerase chain reaction (KASP) markers and an application thereof.

To achieve the above objectives, the present application adopts following technical schemes:
soyasaponin-related KASP markers, where the KASP markers include one or two of S07_43139773G/T and S07_43139033A/G; the S07_43139773G/T includes a base of G/T at a position of 43139773 bp on chromosome 7 of a soybean genome, the S07_43139033A/G include a base of A/G at a position of 43139033 bp on the chromosome 7 of the soybean genome.

Optionally, a soybean with a base G at the S07_43139773G/T is a soybean with low content of saponin Aa, and is a soybean with a high content of saponin Aa with a base T.

Optionally, a soybean with a base A at the S07_43139033A/G is a soybean with high content of saponin Ab, and is a soybean with low content of saponin Ab with a base G.

The present application also provides primer pairs for detecting the KASP markers, where primers pairs of the KASP markers include one or two of a S07_43139773G/T primer pair and a S07_43139033A/G primer pair;
the S07_43139773G/T has an upstream primer F1 with a sequence as shown in SEQ ID No.1, an upstream primer F2 with a sequence as shown in SEQ ID No.2, and a downstream primer R with a sequence as shown in SEQ ID No.3; and
the S07_43139033A/G has an upstream primer F1 with a sequence as shown in SEQ ID No.4, an upstream primer F2 with a sequence as shown in SEQ ID No.5, and a downstream primer R with a sequence as shown in SEQ ID No.6.

The present application also provides a method for screening soybeans with high saponin content, including following steps:
taking a genomic DNA of a soybean to be tested as a template, performing a polymerase chain reaction (PCR) amplification reaction using the primer pairs respectively, and conducting genotyping by fluorescence signals of amplified products of the PCR.

Optionally, if one or two genotypes at the position of 43139773 bp on chromosome 7 of the soybean genome are TT and AA at the position of 43139033 on chromosome 7 of the soybean genome, the soybean to be tested is a soybean with high saponin content.

Compared with the prior art, the present application has the following beneficial effects: according to the soyasaponin-related KASP markers and the application provided by the present application, 264 natural populations of soybean germplasm are subjected to a genome wide association study (GWAS) for the contents of the soyasaponins Aa, Ab, and Bb, and by developing KASP markers using SNP loci significantly related to the two saponin fractions, two KASP markers are designed and obtained; S07_43139773G/T of the present application has an accuracy of 93.2% in detecting soyasaponin content, and S07_43139033A/G of the present application has an accuracy of 93.2% in detecting soyasaponin content, therefore, the KASP markers of the present application are accurate in genotyping soyasaponin content traits, and it is found that the soyasaponin Aa content of the soybean with the S07_43139773G/T genotype of TT is higher than that of GG by genotyping, and the soyasaponin Ab content of the soybean with the S07_43139033A/G genotype of AA is higher than that of GG. Therefore, the KASP markers of the present application are capable of being used in the selective germplasm breeding of soybean with high soyasaponin content, and the KASP markers of the present application are not only highly accurate and less costly, but also simple and efficient in operation, requiring only the extraction of genomic DNA of the plant leaves for PCR amplification.

DETAILED DESCRIPTION OF THE EMBODIMENTS

The present application provides Kompetitive Allele-specific polymerase chain reaction (KASP) markers, where the KASP markers include one or two of S07_43139773G/T and S07_43139033A/G; the S07_43139773G/T includes a base of G/T at a position of 43139773 bp on chromosome 7 of a soybean genome, the S07_43139033A/G includes a base of A/G at a position of 43139033 bp on the chromosome 7 of the soybean genome.

In the present application, when the KASP markers include one or two of S07_43139773G/T and S07_43139033A/G, both of them are related to the content of soyasaponin. In a preferred embodiment, the KASP markers of the present application include preferably one of S07_43139773G/T and S07_43139033A/G. In another preferred embodiment, the KASP markers of the present application are preferably S07_43139773G/T and S07_43139033A/G.

In the present application, at S07_43139773G/T, the soybean with a base G is preferably a soybean with a low content of saponin Aa, and the soybean with a base T is a soybean with high content of saponin Aa. At the S07_43139033A/G, the soybean with a base A is preferably a soybean with high content of saponin Ab, and the soybean with a base G is a soybean with a low content of saponin Ab.

The present application also provides primer pairs for detecting the KASP markers, where the primer pairs of the KASP markers include one or two of a S07_43139773G/T primer pair and a S07_43139033A/G primer pair;

the S07_43139773G/T has an upstream primer F1 with a sequence as shown in SEQ ID No.1, an upstream primer F2 with a sequence as shown in SEQ ID No.2, and a downstream primer R with a sequence as shown in SEQ ID No.3;

the S07_43139033A/G has an upstream primer F1 with a sequence as shown in SEQ ID No.4, an upstream primer F2 with a sequence as shown in SEQ ID No.5, and a downstream primer R with a sequence as shown in SEQ ID No.6.

In the present application, the primer pairs of the KASP markers include one or two of S07_43139773G/T primer pair and S07_43139033A/G primer pair. In a preferred embodiment, the primer pairs of the KASP markers include preferably one of S07_43139773G/T primer pair and S07_43139033A/G primer pair. In another preferred embodiment, the primer pairs of the KASP markers include a S07_43139773G/T primer pair and a S07_43139033A/G primer pair.

Figure 3:
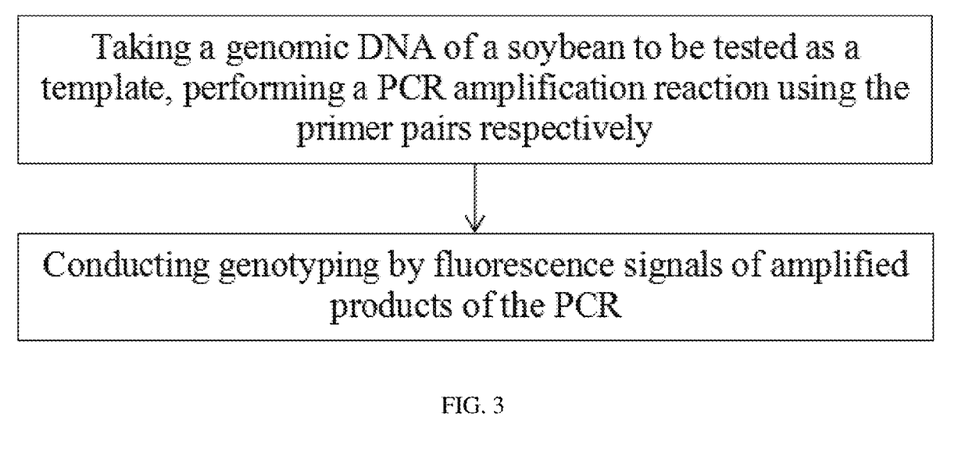
FIG. 3 shows a process of a method for screening soybeans with high saponin content provided by the present application.

The present application also provides a method for screening soybeans with high saponin content, including following steps as shown in FIG. 3:

taking a genomic DNA of a soybean to be tested as a template, performing a PCR amplification reaction using the primer pairs, respectively, and conducting genotyping by fluorescence signals of amplified products of the PCR.

In the present application, if one or two genotypes at the position of 43139773 bp on chromosome 7 in soybean genome are TT and AA at the position of 43139033 on chromosome 7 of the soybean genome, the soybean to be tested is a soybean with high saponin content; and if one or two genotypes at the position of 43139773 bp on chromosome 7 of the soybean genome are GG and GG at the position of 43139033 on chromosome 7 in soybean genome, the soybean to be tested is a soybean with low saponin content.

In the present application, when TT is selected as the genotype at the 43139773 bp position of chromosome 7 in the soybean genome, the soybean to be tested is a soybean with high soyasaponin Aa content; when the genotype GG at the 43139773 bp position of chromosome 7 in the soybean genome is selected, the soybean to be tested is a soybean with low soyasaponin Aa content; and the soybean germplasm with TT genotype has a soyasaponin Aa content higher than GG's. When the genotype AA at the 43139033 bp position of chromosome 7 in the soybean genome is selected, the soybean to be tested is a soybean with high soyasaponin Ab content; when the genotype GG at the 43139033 bp position of chromosome 7 in the soybean genome is selected, the soybean to be tested is a soybean with low soyasaponin Ab content, where the soybean germplasm with genotype AA has higher soyasaponin Ab content than GG's. In the present application, when the genotypes at the 43139773 bp position and the 43139033 bp of chromosome 7 in the soybean genome are TT and AA respectively, the soyasaponin content of the soybean to be detected is significantly improved.

In the present application, the genomic DNA of the soybean to be detected is used as a template, and PCR amplification reactions are respectively performed by using the primer pairs. The PCR amplification preferably includes a system of 5 microliters (μL) of 45-55 nanograms per microliter (ng/μL) soybean sample DNA template, 5 μL of 2×KASPMastermix, and 0.14 μL of KASP AssayMix (F1: F2:R=1:1:1). The reaction conditions of KASP-PCR amplification are as follows: 94 degrees Celsius (° C.) for 15 minutes (min) in the first stage; 94° C. for 20 seconds (s) and 61-55° C. for 1 min in the second stage, with the annealing temperature reduced by 0.6° C. in each cycle, for a total of 10 cycles; 94° C. for 20 s and 55° C. for 1 min in the third stage, for a total of 26 cycles; and 37° C. for 1 min in the fourth stage.

The technical schemes provided by the present application are described in detail below in connection with the embodiments, but they are not to be construed as limiting the scope of protection of the present application.

Embodiment 1

(1) Genome wide association study (GWAS) of soyasaponin: the SNP markers used in GWAS of natural populations are derived from the resequencing effort, a high-density physical map containing a total of 2,597,425 SNPs; the GWAS is conducted using the GAPIT algorithm package based on R software for computation, and mixed linear model (MLM) for GWAS to control for false-positive association loci; the threshold of significance is $P \leq 1/2597425 = 3.85 \times 10^{-7}$, $-\text{Log } P \geq 6.4$, and SNPs are considered to be significantly associated loci when they have a $-\text{Log } P \geq 6.4$, whereas SNPs are considered to be potentially associated loci when the threshold is at $5 \leftarrow \text{Log } P < 6.4$.

High performance Liquid Chromatography (HPLC) is used to detect the soyasaponin content of natural soybean populations harvested in 2020 at the Hainan base and in 2021 at the Liuhe base in Nanjing, respectively, then GWAS is conducted on the data of soyasaponin content phenotypes of the two years, with visualization results as shown in FIG. 1A-FIG. 1H.

An Agilent 1260 HPLC is used for the determination of soyasaponin content, the detector is an evaporative light scattering detector (ELSD), and the determination steps of soyasaponin content are as follows:

(1) Preparation of Soyasaponin Standard Sample four kinds of soyasaponin standard each 0.01 gram (g) (accurate to 0.0001 g) are weighed, configured into a mother liquor of 1 milligram per milliliter (mg/mL) with methanol (chromatographic purity), and then subjected to a gradient dilution with concentrations of 0.6 mg/mL, 0.5 mg/mL, 0.4 mg/mL, 0.3 mg/mL, 0.2 mg/mL, 0.1 mg/mL, 0.08 mg/mL, 0.08 mg/mL, 0.04 mg/mL, and 0.02 mg/mL, then passed through a 0.22 micrometer (m) membrane for later use, and the soyasaponin standard solution should be prepared freshly and used immediately;

(2) Extraction of Soyasaponin the collected soybean seeds are put into an oven to be dried to constant weight at 80° C., and then fully ground into powder by a plant tissue grinding instrument; 1 g (accurate to 0.01 g) of soybean powder is accurately weighed and put into a 15 mL centrifuge tube, added with 10 mL of 70% (V/V) ethanol aqueous solution, and then extracted by ultrasonic bath at 40° C. for 40 min (40 kilohertz, kHz), during which the centrifuge tube is occasionally shaken in order to sufficiently extract the saponins; the centrifuge tube is then centrifuged at 3,000 revolutions per minute (rpm) for 5 min, and the supernatant is sucked up with a 1 mL syringe and filtered through a 0.22 μm membrane into a sample bottle, then put into a refrigerator at −20° C. for later use;

(3) HPLC Detection the chromatographic conditions of HPLC are as follows: chromatographic column: Thermo BDS Hypersil C18 (250 mm×4.6 mm, 5 m); mobile phase A: 0.2% (V/V) aqueous acetic acid solution, mobile phase B: 100% (V/V) acetonitrile solution; flow rate: 1.0 mL/min; column temperature: 30° C.; injecting volume: 10 μL; the eluting procedure of HPLC is shown in Table 1; three repetitive injections are carried out for each sample, the content of soyasaponin components in the sample is calculated according to the standard curve drawn by the standard product, and the average value of the three injections is taken as the final test result of soyasaponin components.

TABLE 1

HPLC elution procedure

| Time (t/min) | | 0 | 15 | 20 |
|---|---|---|---|---|
| Mobile phase concentration | A (%) | 80 | 55 | 55 |
| Mobile phase concentration | B (%) | 20 | 45 | 45 |

TABLE 2

Number of SNP loci associated with soyasaponin in natural populations

| Saponin component | Year | $-\log_{10}(P) \geq 6.4$ | $5 \leq -\log_{10}(P) < 6.4$ | $-\log_{10}(P) \geq 5$ |
|---|---|---|---|---|
| Soyasaponin Aa | 2020 | 1163 | 287 | 1450 |
|  | 2021 | 1345 | 333 | 1678 |
| Soyasaponin Ab | 2020 | 818 | 513 | 1331 |
|  | 2021 | 229 | 147 | 376 |
| Soyasaponin Bb | 2020 | 0 | 10 | 10 |
|  | 2021 | 4 | 39 | 43 |

The results in Table 2, FIG. 1A to FIG. 1H show that there are 1,450 SNPs associated with soyasaponin Aa ($-\log_{10}(P) \geq 5$) in Hainan in 2020, and 1,163 SNPs with significant association ($-\log_{10}(P) \geq 6.4$), which are distributed on chromosomes 2, 7 and 17 respectively, and 1,331 SNPs associated with soyasaponin Ab, and 818 SNPs are significantly associated, distributed on chromosome 7; there are only 10 SNPs associated with Bb, yet with no significant correlation site; and in 2021, there are a total of 1,678 SNPs associated with soyasaponin Aa in Nanjing, with a total of 1,345 significantly associated SNPs, 182 SNPs more than that in 2020, distributed on chromosomes 7, 9, and 14. In contrast, the situation of soyasaponin Ab is different from that of soyasaponin Aa; compared with 2020, the number of significantly associated SNPs for soyasaponin Ab is 229, 589 fewer instead, which are distributed on chromosomes 7 and 9, respectively; it is worth noting that in 2021, soyasaponin Bb has 4 more significantly associated SNP sites than in 2020, and there are 2 significant sites on chromosomes 5 and 14, respectively (see Table 2).

TABLE 3

SNPs significantly related to each saponin

| Year | Location | Saponin component | Chromosome | SNP number | Position interval | Peak SNP position | $(-\log_{10}P_{max})$ |
|---|---|---|---|---|---|---|---|
| 2020 | Sanya | Aa | 2 | 2 | 25855572-25855573 | 25855573 | 7.18 |
| | | Aa | 7 | 1159 | 25192890-43690399 | 43139773 | 10.63 |
| | | Aa | 17 | 2 | 25192890-35737828 | 35737828 | 7.85 |
| | | Ab | 7 | 818 | 42687402-43773327 | 43139612 | 13.44 |
| 2021 | Nanjing | Aa | 7 | 1343 | 5260351-43918953 | 43918953 | 13.26 |
| | | Aa | 9 | 1 | 23186063 | 23186063 | 7.27 |
| | | Aa | 14 | 1 | 36847880 | 36847880 | 7.52 |
| | | Ab | 7 | 227 | 43113840-43217800 | 43217800 | 8.72 |
| | | Ab | 9 | 2 | 39078161-39078180 | 39078180 | 6.81 |
| | | Bb | 5 | 2 | 1042162-33311337 | 33311337 | 7.66 |
| | | Bb | 14 | 2 | 4124002-4225806 | 4225806 | 7.60 |

As can be seen from Table 3, the peak SNP positions of soyasaponins Aa and Ab in Sanya in 2020 are located at chromosome 7, at 43139773 bp and 43139612 bp, respectively, with the maximum values of $-\log_{10}(P)$ being 10.63 and 13.44, respectively; in Nanjing 2021, the peak SNP positions of soyasaponins Aa and Ab are both on chromosome 7, located at chromosome S07, at chromosome 43918953 bp and 43217800 bp, with maximum values of $-\log_{10}(P)$ being 13.26 and 8.72, respectively, and the soyasaponin Bb is at 33311337 on chromosome S05, with a maximum value of $-\log_{10}(P)$ of 7.66.

TABLE 4

Number of SNP common sites associated with soyasaponin in natural populations in the two years

| Saponin component | Chromosome | $-\log_{10}(P) \geq 6.4$ | $5 \leq -\log_{10}(P) < 6.4$ | $-\log_{10}(P) \geq 5$ |
|---|---|---|---|---|
| Soyasaponin Aa | 7 | 928 | 25 | 1306 |
| Soyasaponin Ab | 7 | 227 | 1 | 301 |

The results in Table 4 show that there are many co-locations of SNP loci associated with soyasaponins in the natural populations in 2020 and 2021, and in both years the SNP co-locations of soyasaponins Aa and Ab are located on chromosome 7, being 1,306 and 301, respectively, and the SNP co-locations of significant associations ($-\log_{10}(P)\geq 6.4$) are 928 and 227, respectively, but there is no co-location of soyasaponins Bb.

Embodiment 2

Soyasaponin-related KASP markers, where the KASP markers are S07_43139773G/T and S07_43139033A/G.

Each pair of primers includes two specific forward primers F1 and F2 and a universal reverse primer R, where the F1 and F2 respectively contain fluorescent linker sequences (underlined) of 6-carboxyfluorescein (FAM) and hexachloro-6-methylfluorescein (HEX), the primer sequences are synthesized by Tsingke Biotech (Nanjing), and the sequences are shown in Table 5.

TABLE 5

Specific primers for KASP markers

| SNP | Primer name | | Primer sequence |
|---|---|---|---|
| S07_43139773 | SEQ ID No. 1 | F1 | <u>GAAGGTGACCAAGTTCATGCT</u>TCCTCATCCTGGCCCACCCG |
| | SEQ ID No. 2 | F2 | <u>GAAGGTCGGAGTCAACGGATT</u>TCCTCATCCTGGCCCACCCT |
| | SEQ ID No. 3 | R | CGGCGTCTGATGTTTTGAGC |
| S07_43139033 | SEQ ID No. 4 | F1 | <u>GAAGGTGACCAAGTTCATGCT</u>AGCCGCCATGCTCCTCCGCA |
| | SEQ ID No. 5 | F2 | <u>GAAGGTCGGAGTCAACGGATT</u>AGCCGCCATGCTCCTCCGCG |
| | SEQ ID No. 6 | R | ATGATCCATGAAGGCGGTGG |

Embodiment 3

Soyasaponin-related KASP markers, where the KASP markers include S07_43139773G/T.

The primer pairs of KASP markers include two specific forward primers F1 and F2 and a universal reverse primer R, where the F1 and F2 respectively contain fluorescent linker sequences (underlined) of 6-carboxyfluorescein (FAM) and hexachloro-6-methylfluorescein (HEX), the primer sequences are synthesized by Tsingke Biotech (Nanjing), and the upstream primer F1, the upstream primer F2 and the downstream primer R have sequences as shown in SEQ ID No.1, SEQ ID No.2, and SEQ ID No.3 respectively.

Embodiment 4

Soyasaponin-related KASP markers, where the KASP markers include S07_43139033A/G.

The primer pairs of KASP markers include two specific forward primers F1 and F2 and a universal reverse primer R, where the F1 and F2 respectively contain fluorescent linker sequences (underlined) of 6-carboxyfluorescein (FAM) and hexachloro-6-methylfluorescein (HEX), the primer sequences are synthesized by Tsingke Biotech (Nanjing), and the upstream primer F1, the upstream primer F2 and the downstream primer R have sequences as shown in SEQ ID No.4, SEQ ID No.5, and SEQ ID No.6 respectively.

Embodiment 5

Soyasaponin-related KASP markers, where the KASP markers are S07_43139773G/T and S07_43139033A/G.

The primer pairs of KASP markers include two specific forward primers F1 and F2 and a universal reverse primer R, where the F1 and F2 respectively contain fluorescent linker sequences (underlined) of 6-carboxyfluorescein (FAM) and hexachloro-6-methylfluorescein (HEX), the primer sequences are synthesized by Tsingke Biotech (Nanjing), and the upstream primer F1, the upstream primer F2 and the downstream primer R have sequences as shown in SEQ ID No.1, SEQ ID No.2, SEQ ID No.3, SEQ ID No.4, SEQ ID No.5, and SEQ ID No.6 respectively.

Embodiment 6

A method for screening soybeans with high saponin content, including following steps:
1) extraction of DNA of the soybean to be detected
fresh soybean leaves sown at R6 stage in the base are picked and put into a 2 mL centrifuge tube with small steel balls at the bottom, then frozen in liquid nitrogen or a foam box with ice boxes, and preserved for genomic DNA extraction;
the DNA of soybean leaves is extracted by the cetyltrimethylammonium bromide (CTAB) method, and the configuration system of 100 mL 2×CTAB buffer is shown in Table 6.

TABLE 6

| DNA extraction system ||| 
|---|---|---|
| Component | Concentration | Usage |
| CTAB | 3% | 3 g |
| PVP | 2% | 2 g |
| β-mercaptoethanal | 2% | 2 mL |
| 1 mM Tris-HCL (PH 8.0) | 100 mM | 10 mL |

TABLE 6-continued

| DNA extraction system ||| 
|---|---|---|
| Component | Concentration | Usage |
| 5M NaCl | 1.4M | 28 mL |
| 0.5M EDTA | 20 mM | 4 mL |
| dH$_2$O | | up to 100 |

After configuring the DNA extraction solution, the specific procedure for DNA extraction is shown below:
(1) the 2×CTAB buffer is taken to a fume hood to be added with 2% (3-mercaptoethanal, and 200 μL of β-mercaptoethanal is added for every 10 mL of CTAB;
(2) the 2 mL centrifuge tube into which the sample was collected earlier is frozen in liquid nitrogen together with a grinding cassette, with the nitrogen just covering the cassette;
(3) the centrifuge tube is symmetrically placed into the sample grinding box and then placed into the plant tissue grinder for grinding, the plant tissue is ground at 40 kHz for 30 s, and after the grinding is completed, the sample is placed into the liquid nitrogen again;
(4) the sample is brought to the fume hood and added with 600 μL of 2×CTAB buffer, which is quickly covered and mixed;
(5) water bath is performed at 65° C. for half an hour, and the centrifuge tube is shaken every 5 min;
(6) at the end of the water bath, the sample is brought to the fume hood for the first extraction, and an equal volume of nucleic acid extraction solution (chloroform: isoamyl alcohol of 24:1) is added, mixed by turning up and down, and shaken for 3 to 5 min;
(7) the sample is centrifuged at 10,000 r/min for 5 min and 600 μL of supernatant is aspirated into a new 1.5 mL centrifuge tube;
(8) the sample from the previous step is brought to the fume hood for the second extraction, and an equal volume of nucleic acid extraction solution (chloroform: isoamyl alcohol of 24:1) is added, mixed by turning up and down;
(9) then it is centrifuged at 10,000 r/min for 5 min and 400 μL of supernatant is aspirated into a new 1.5 mL centrifuge tube;
(10) 20 μL of 5 molarity (M) NaCl is added to the centrifuge tube, then 400 μL of isopropanol pre-cooled in a −20° C. refrigerator is added, gently mixed, and placed in a −20° C. refrigerator for more than 30 min;
(11) the centrifuge tube is centrifuged at 12,000 r/min for 5 min and the waste liquid is poured off;
(12) 600 μL of 70% ethanol is added and the precipitate is flicked up with a finger, followed by centrifugation at 12,000 r/min for 5 min before pouring off the waste liquid; and
(13) the step (12) is repeated once and then the centrifuge tube is left at room temperature overnight, the next day, 50 μL of water is added for dissolution, and then it is placed in a −20° C. refrigerator for long-term storage.

The concentration of extracted DNA is detected with a nucleic acid protein detector, and then the spare DNA is diluted to 50 ng/μL with ultrapure water.

KASP markers are developed for SNP loci S07_43139773 (G/T) and S07_43139033 (A/G), which are significantly associated with soyasaponins Aa, Ab, and Bb, and the marker sequences are shown in Table 5, and the DNA of soybean genome extracted from step 1) is used as the template, then PCR amplification is carried out with the corresponding primers F1, F2, and R, respectively, and the reaction is carried out in a QuantStudio5 real-time fluorescence quantitative PCR instrument to obtain the PCR amplification products, where the PCR amplification system is as follows: a total volume of 10 μL, including soybean sample DNA template (50 ng/μL) 5 μL, 2×KASP Mastermix 5 μL, primer mixture 0.14 μL; PCR reaction conditions are: 94° C. for 15 min at the first stage, 94° C. for 15 min in the first stage, 94° C. for 20 s in the second stage, 61-55° C. for 1 min, with the annealing temperature decreasing by 0.6° C. in each cycle, for a total of 10 cycles, 94° C. for 20 s in the third stage, 55° C. for 1 min, for a total of 26 cycles, and 37° C. for 1 min in the fourth stage.

After the reaction is over, the fluorescence data of the reaction products are read on the QuantStudio5 real-time fluorescence quantitative PCR instrument, and the 24 soybeans are amplified and genotyped on the real-time fluorescence quantitative PCR instrument using KASP molecular marker primers.

TABLE 7

Saponin content of soybean germplasm with different genotypes

| Saponin component | SNP | Genotype | Mean saponin content 2020 | 2021 |
|---|---|---|---|---|
| Soyasaponin Aa | S07_43139773 | GG | 0.107 | 0.276 |
| | | TT | 0.278 | 0.636 |
| Soyasaponin Ab | S07_43139033 | AA | 0.367 | 0.491 |
| | | GG | 0.132 | 0.149 |
| Soyasaponin Bb | S14_6332401 | TT | 0.244 | 0.157 |
| | | CC | 0.257 | 0.167 |

Figure 1A:
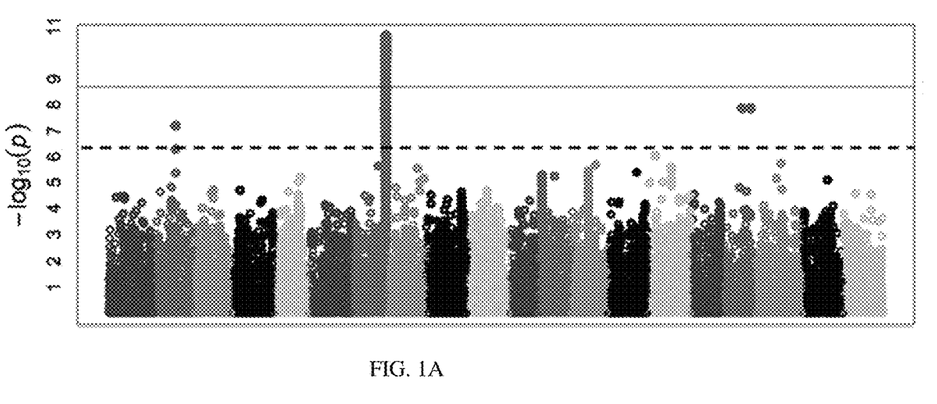
FIG. 1A shows a Manhattan plot of results of genome wide association study (GWAS) for Hainan soyasaponin Aa in 2020.
Figure 1B:
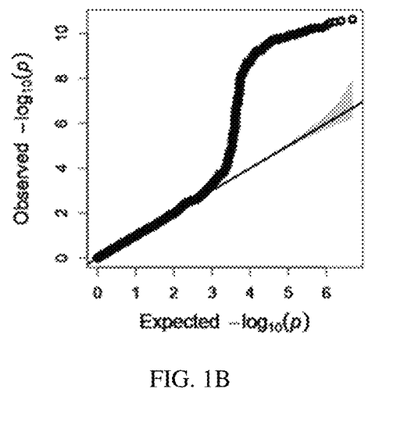
FIG. 1B shows a quantile-quantile (QQ) plot of results of GWAS for Hainan soyasaponin Aa in 2020.
Figure 1C:
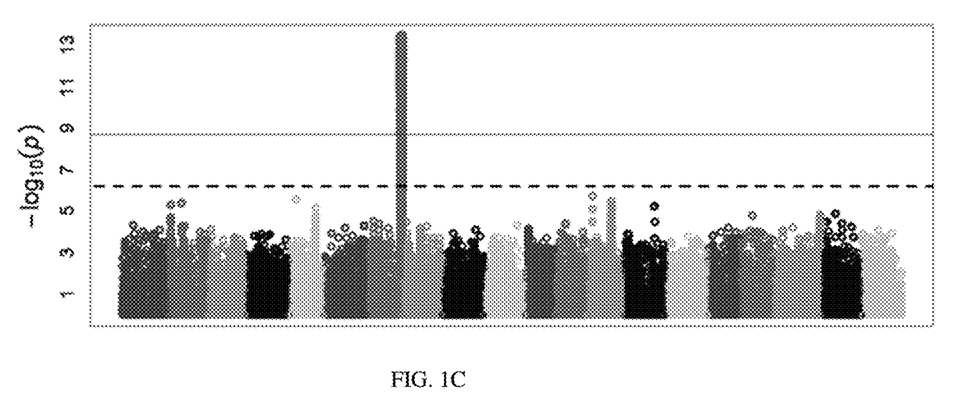
FIG. 1C shows a Manhattan plot of results of GWAS for Hainan soyasaponin Ab in 2020.
Figure 1D:
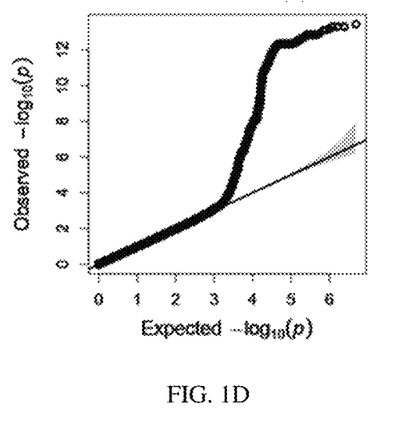
FIG. 1D shows a QQ plot of results of GWAS for Hainan soyasaponin Ab in 2020.
Figure 1E:
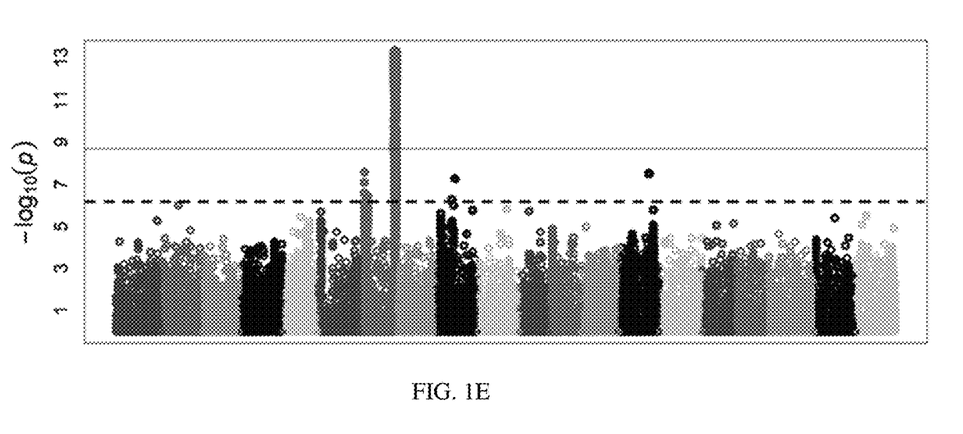
FIG. 1E shows a Manhattan plot of results of GWAS for Nanjing soyasaponin Aa in 2020.
Figure 1F:
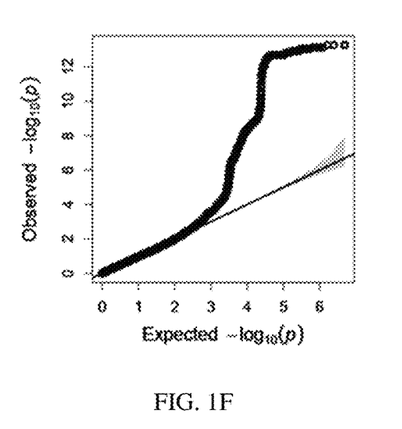
FIG. 1F shows a QQ plot of results of GWAS for Nanjing soyasaponin Aa in 2020.
Figure 1G:
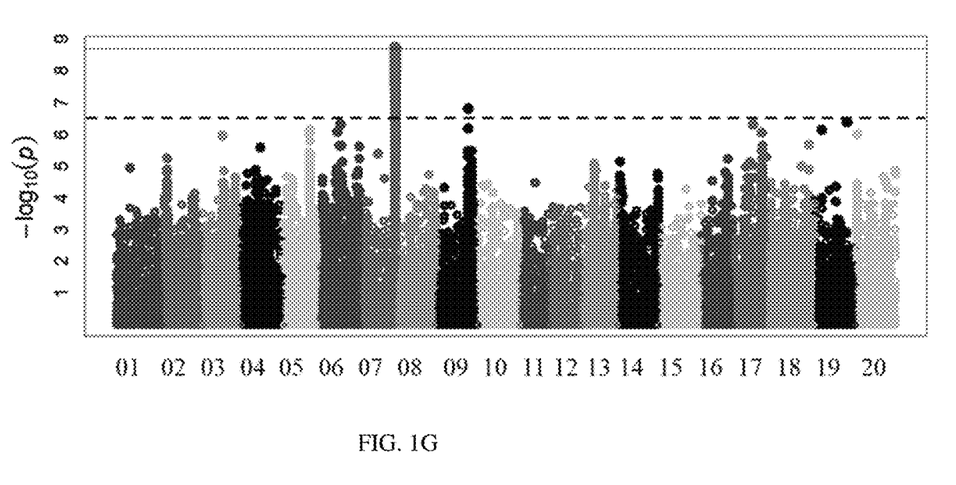
FIG. 1G shows a Manhattan plot of results of GWAS for Nanjing soyasaponin Ab in 2020.
Figure 1H:
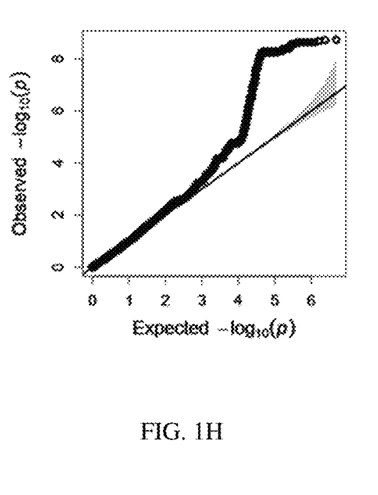
FIG. 1H shows a QQ plot of results of GWAS for Nanjing soyasaponin Ab in 2020.
Figure 2A:
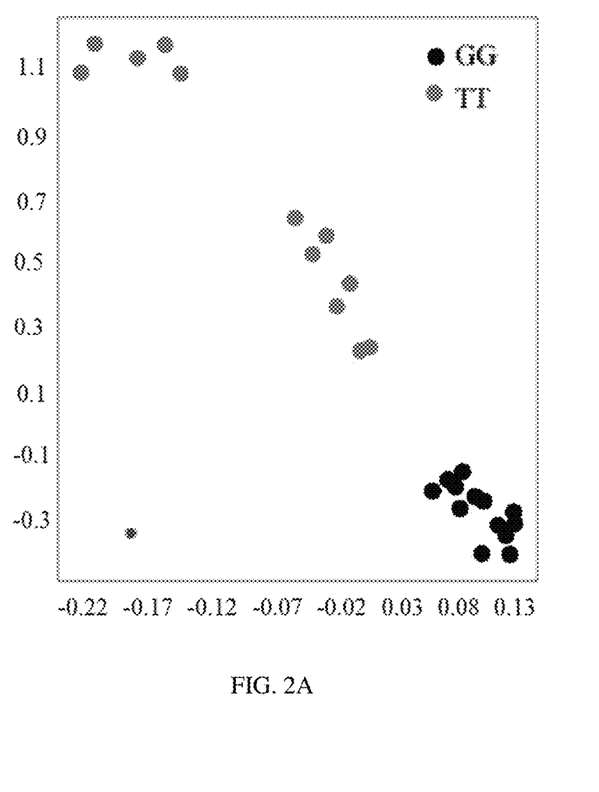
FIG. 2A shows genotyping results of Kompetitive Allele-specific polymerase chain reaction (KASP) marker of S07_43139773.
Figure 2B:
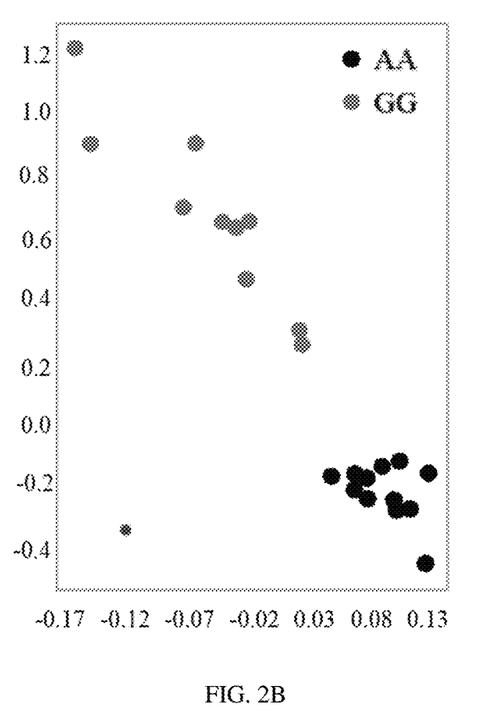
FIG. 2B shows genotyping results of KASP marker of S07_43139033.

The results in FIG. 2A and FIG. 2B indicate that both molecular marker primer pairs are capable of clearly separating the two genotypes.

As can be seen from the FIG. 2A, FIG. 2B and Table 7, the results show that for the S07_43139773G/T, the KASP markers designed for SNP markers significantly associated with soysaponin Aa, the grey dots near the Y-axis are soybean varieties with high saponin content that carry the T allele locus, and the black dots near the X-axis are soybean varieties with low saponin content that carry the G allele locus, and the black dot near the origin of coordinate axes is the blank control. The soybean varieties with genotype TT have a higher content of soyasaponin Aa than that of GG's in both years, and the content of soyasaponin Aa is increased by 159.02% and 94.47% respectively.

As for the S07_43139033A/G, the KASP markers designed for SNP markers significantly associated with soysaponin Ab, the grey dots near the Y-axis are the soybean varieties with low saponin content carrying the G allelic variant locus, the black dots near the X-axis are the soybean varieties with high saponin content carrying the A allelic variant locus, and the black dot near the origin is the blank control. The soybean varieties with genotype AA offer greater soyasaponin Ab content than that of GG in both years, and the soyasaponin Ab content is increased by 177.84% and 230.38% respectively.

In this application, GWAS is performed on 264 natural populations of soybean germplasm for the content of soyasaponins Aa, Ab, and Bb, enabling more reliable SNP loci of soyasaponins obtained from the association analysis, and more accurate exploitation of soyasaponins candidate genes and the development of genetic markers. Moreover, the KASP markers are developed using SNP sites that are significantly related to the two saponin components, and the KASP markers of the present application are not only highly accurate and less costly, but also simple and convenient, providing a basis for further research on soyasaponin-related genes and screening of soybean with high saponin content, as well as molecular markers for assisted breeding of soybeans.

The foregoing describes only preferred embodiments of the present application, and it should be noted that for a person of ordinary skill in the art, a number of improvements and modifications are also available without departing from the principles of the present application, which should also fall in the scope of protection of the present application.

What is claimed is:

1. Primer pairs for detecting soyasaponin-related allele-specific PCR markers, wherein the allele-specific PCR markers comprise one or both of S07_43139773G/T and S07_43139033A/G; wherein the S07_43139773G/T comprises a base of G/T at a position of 43139773 bp on chromosome 7 of the soybean genome, and the S07_43139033A/G comprises a base of A/G at a position of 43139033 bp on the chromosome 7 of the soybean genome;
   wherein primer pairs of the allele-specific PCR markers comprise one or both of a S07_43139773G/T primer pair and a S07_43139033A/G primer pair;
   wherein the S07_43139773G/T has an upstream primer F1 with a sequence as shown in SEQ ID No.1, an upstream primer F2 with a sequence as shown in SEQ ID No.2, and a downstream primer R with a sequence as shown in SEQ ID No.3; and/or
   wherein the S07_43139033A/G has an upstream primer F1 with a sequence as shown in SEQ ID No.4, an upstream primer F2 with a sequence as shown in SEQ ID No.5, and a downstream primer R with a sequence as shown in SEQ ID No.6.

* * * * *

SEQUENCE LISTING

```
Sequence total quantity: 6
SEQ ID NO: 1              moltype = DNA   length = 41
FEATURE                   Location/Qualifiers
source                    1..41
                          mol_type = other DNA
                          organism = synthetic construct
SEQUENCE: 1
gaaggtgacc aagttcatgc ttcctcatcc tggcccaccc g               41

SEQ ID NO: 2              moltype = DNA   length = 41
FEATURE                   Location/Qualifiers
source                    1..41
                          mol_type = other DNA
                          organism = synthetic construct
SEQUENCE: 2
gaaggtcgga gtcaacggat ttcctcatcc tggcccaccc t               41

SEQ ID NO: 3              moltype = DNA   length = 20
FEATURE                   Location/Qualifiers
source                    1..20
                          mol_type = other DNA
                          organism = synthetic construct
SEQUENCE: 3
cggcgtctga tgttttgagc                                       20

SEQ ID NO: 4              moltype = DNA   length = 41
FEATURE                   Location/Qualifiers
```

```
source                  1..41
                        mol_type = other DNA
                        organism = synthetic construct
SEQUENCE: 4
gaaggtgacc aagttcatgc tagccgccat gctcctccgc a            41

SEQ ID NO: 5            moltype = DNA  length = 41
FEATURE                 Location/Qualifiers
source                  1..41
                        mol_type = other DNA
                        organism = synthetic construct
SEQUENCE: 5
gaaggtcgga gtcaacggat tagccgccat gctcctccgc g            41

SEQ ID NO: 6            moltype = DNA  length = 20
FEATURE                 Location/Qualifiers
source                  1..20
                        mol_type = other DNA
                        organism = synthetic construct
SEQUENCE: 6
atgatccatg aaggcggtgg                                    20
```